United States Patent [19]

Smith et al.

[11] Patent Number: 5,536,943

[45] Date of Patent: Jul. 16, 1996

[54] METHOD AND APPARATUS FOR EXAMINING AN OBJECT

[75] Inventors: Martin P. Smith, Berkshire; Christopher M. Welbourn, Waltham-St-Lawrence, both of England

[73] Assignee: Gersan Establishment, Vaduz, Liechtenstein

[21] Appl. No.: 341,532

[22] PCT Filed: May 19, 1993

[86] PCT No.: PCT/GB93/01024

§ 371 Date: Feb. 13, 1995

§ 102(e) Date: Feb. 13, 1995

[87] PCT Pub. No.: WO93/23742

PCT Pub. Date: Nov. 25, 1993

[30] Foreign Application Priority Data

May 19, 1992 [GB] United Kingdom ............ 9210674

[51] Int. Cl.$^6$ .................................................. G01N 21/87
[52] U.S. Cl. .......................... 250/372; 250/358.1; 356/30
[58] Field of Search .................................. 250/347, 353, 250/358.1, 372, 373, 461.1, 458.1; 356/30

[56] References Cited

U.S. PATENT DOCUMENTS

| | | | |
|---|---|---|---|
| 4,236,076 | 11/1980 | Judge et al. | 250/347 |
| 4,291,975 | 9/1981 | Raccah. | |
| 4,394,580 | 7/1983 | Gielissa | 250/461.1 |
| 4,511,800 | 4/1985 | Harbeke et al. | 250/358.1 X |
| 4,578,762 | 3/1986 | Wong. | |
| 5,028,800 | 7/1991 | Wulf et al.. | |

FOREIGN PATENT DOCUMENTS

| | | |
|---|---|---|
| 0412410 | 2/1991 | European Pat. Off. . |
| 2528580 | 12/1983 | France . |
| 1207113 | 12/1969 | Germany . |
| 1254316 | 11/1971 | United Kingdom . |
| 1531844 | 11/1978 | United Kingdom . |
| 2045426 | 10/1980 | United Kingdom . |
| 2113829 | 8/1983 | United Kingdom . |
| 2182785 | 5/1987 | United Kingdom . |
| WO83/00389 | 2/1983 | WIPO . |
| WO91/16617 | 10/1991 | WIPO . |

OTHER PUBLICATIONS

Extract from GEM Testing (Tenth Edition) by B. W. Anderson and E. J. Jobbins, Preface and pp. 96–97, 124–125, and 202–205.

Primary Examiner—Carolyn E. Fields
Assistant Examiner—Edward J. Glick
Attorney, Agent, or Firm—Rosen, Dainow & Jacobs

[57] ABSTRACT

In order to examine an object with radiation and measure the intensity of radiation used to illuminate the object, radiation is directed onto a wavelength selective mirror (31). In a first position, the mirror (31) reflects the illuminating radiation to a beam splitter (30) which passes the radiation to a detector (34). In a second position the mirror (31) directs the radiation to an object (33), radiation of the selected wavelength emanating from the object being reflected by the mirror via beam splitter (30) to the detector (34). The mirror (31) is rotated between the first and second position. In order to classify a diamond as natural or synthetic, a first signal is derived dependent upon the intensity of ultra-violet radiation transmitted by the diamond at 254 nm, and a second signal is derived dependent upon the intensity of radiation transmitted by the diamond at 365 nm and the diamond is classified as being definitely natural if the first signal is substantially greater than the second signal.

32 Claims, 2 Drawing Sheets 5,536,943

METHOD AND APPARATUS FOR EXAMINING AN OBJECT

BACKGROUND OF THE INVENTION

This invention relates to a method and apparatus for examining objects by irradiating them with radiation and analyzing the transmitted or emitted radiation. The invention also relates to a method and apparatus for classifying diamonds.

Normally, apparatus for examining objects using radiation comprises a source, which may be a laser of a particular wavelength or a broad-band illuminator such as a tungsten lamp, means for controllably exposing the object to the radiation and means for collecting radiation transmitted or emitted by the object. The transmitted or emitted radiation may be filtered to exclude the illuminating wavelength or to transmit a single wavelength of interest, the radiation passed by the filter being passed to a detector.

Such an apparatus may be used for examining diamonds, the information obtained depending on the wavelength of radiation studied.

It is desired to provide a method and apparatus for examining objects in which the intensity of the irradiating radiation may be measured, the path for measuring the irradiating radiation being as similar as possible to the path of the radiation to the object. Furthermore, it is desired to minimize the number of parts required and to simplify the apparatus generally.

THE INVENTION

The first aspect of the invention provides apparatus for and a method of examining an object. The method and apparatus of the first aspect of the invention allow the intensity of radiation used to irradiate the object to be detected. Accordingly, temperature variations or other variations in the spectrum of the radiation source can be allowed for when interpreting the results. The apparatus can be small and simple. The same reflective member is used in the path of radiation from the sample to the detector and the source to the detector.

In the second position of the reflective member, a signal can be produced dependent upon the intensity of light which is reflected by the object, transmitted by the object, reflected through the object or emitted by the object by luminescence.

The radiation path from the source to the reflective member, from the reflective member to the object or from the reflective member to the detector is preferably as simple as possible, involving the smallest number of optical elements, to reduce the amount of radiation lost at each optical element. However, any radiation path may be used and may comprise a plurality of reflective devices. The reflective member may comprise a plurality of components but the change from the first position to the second position is achieved in this case substantially by changing the position of the reflective member as a whole or as a unit.

For simplicity, only one reflective member should be used. This is possible, because the apparatus can be set up such that radiation directed to the object and (a portion of) the radiation emanating from the object intersect the same reflective member. Preferably, the path of irradiating radiation is coincident with the path of radiation emanating from the object which intersects the reflective member. In this case, a beam splitter may be used to direct light to the detector.

Using the beam splitter allows the apparatus to be set up very simply, as it uses the principle of reversability of light. Whatever path the irradiating radiation takes (reflected back by the reflective member or reflected onto the sample), reflected radiation must be able to travel back along the path of the irradiating radiation. It will then be interrupted by the beam splitter and so directed to the detector.

The beam splitter is preferably placed before the reflective member in the path of radiation coming from a source, the radiation coming from the source not being directed to the detector by the beam splitter. In this configuration, the first position of the reflective member may correspond to the reflective member being normal to the direction of radiation from the source so that the radiation is reflected back onto the beam splitter which will then deflect the beam of radiation to the detector.

Other radiation paths may be chosen if necessary, for example a further mirror may be provided to reflect radiation back to the reflective means when in the first position.

In the simplest arrangement, the reflective member is moved and the input beam and the detector means are stationary with respect to one another. However, it would be possible to keep the beam of input radiation stationary with respect to the reflective means and to move the two parts together with respect to the detector.

The detector is preferably a photomultiplier tube, but may be any convenient form of radiation detecting means. Preferably, the detector gives a signal dependent upon the intensity of light incident upon it.

The reflective member can be mounted for rotation about an axis. This allows it to be flipped or moved quickly between the first and second position. It also facilitates taking a large number of measurements using the apparatus, by rotating the reflective member and cycling through the positions at great speed.

A polychromatic or broad band radiation source can be used easily with the present invention, which is cheaper than a laser.

The reflective member is preferably a wavelength selective mirror. This allows the apparatus to be particularly simple because a single part of the apparatus is used to selectively direct radiation in different paths and to select the radiation directed.

Preferably, two or more wavelengths may be measured by providing a second wavelength selective, reflective surface on the reflective member, for instance on the reverse side. A wavelength selective mirror having two separate wavelength selective mirrors back to back or two separate wavelength selective mirrors mounted at different positions on a rotating mount may be used.

In order to study the intensity of radiation transmitted by the object at the input wavelength, the object may be placed in an irradiation zone comprising further reflective means for reflecting radiation transmitted by the object back in the direction of the input radiation back to the reflective member. For example, an integrating sphere may be used. If the object is a cut brilliant diamond, reflective means are not required. The radiation is input through the table of the diamond and the diamond is cut such that a large proportion of light entering the diamond through the table is transmitted by the diamond and reflected out through the table.

The second aspect of the invention provides a method of and apparatus for classifying a diamond. The second aspect of the invention allows the different ultra-violet absorption characteristics of different types of diamond (e.g. type IaAB, type II etc.) to be used to classify a given diamond. All diamonds show strong absorption of short wave ultra-violet radiation at wavelengths less than a certain cut-off wavelength which varies from type to type.

Below the cut-off wavelength, the diamond effectively becomes opaque to the radiation.

In the second aspect of the invention, a diamond may be classified as belonging to one of two types, which are distinguished by their absorption cut-off wavelengths. A measurement of the fraction of incident radiation absorbed (or, equally, transmitted) is made at a value between the two cut-off wavelengths. The diamond will either show very strong absorption (if it belongs to the type whose cut-off wavelength is higher than the test wavelength) or moderate absorption (if the cut-off wavelength is less than the test wavelength).

The measurement of the absorption at a wavelength between the two cut-off wavelengths should be normalized to allow for the size of the diamond. Any suitable normalizing means may be used, for example a signal may be derived or input based upon the size of the diamond. The first signal can be corrected by dividing it by the size signal.

Preferably, a further measurement should also be made at a further ultra-violet wavelength at which all types of diamond are likely to show only moderate absorption in order to provide a signal dependent upon the size of the object as a size reference for the signal.

Preferably, the first class of diamonds comprises diamonds of type IaAB which show strong absorption below about 290 nm. The second class may comprise all other types of diamond, which will have strong absorptions below about 225 nm. The test measurement is made at a value between 225 and 290 nm and the further measurement is taken at a wavelength greater than 290 nm. Preferably, a mercury lamp is used to produce the ultra-violet radiation. Radiation produced by a mercury lamp has strong bands at 254 nm and 365 nm. These clearly fit the requirements for test and further wavelengths set out above. Thus, using a single source, both the test and further wavelengths may be produced.

Preferably, the second aspect of the invention is used with the first aspect of the invention. Preferably, a wavelength selective mirror having two wavelength selective faces is provided, for selecting the 254 nm band and 365 nm band respectively. Radiation is fed through the table of the diamond (if it is a brilliant cut diamond) and a substantial quantity of radiation entering the diamond will be reflected through the diamond and transmitted through the table of the diamond. This transmitted radiation is directed by the reflective member to the detector.

The invention will be further described with reference to the accompanying drawings, in which:

DETAILED DESCRIPTION OF THE DRAWINGS

Figure 1:
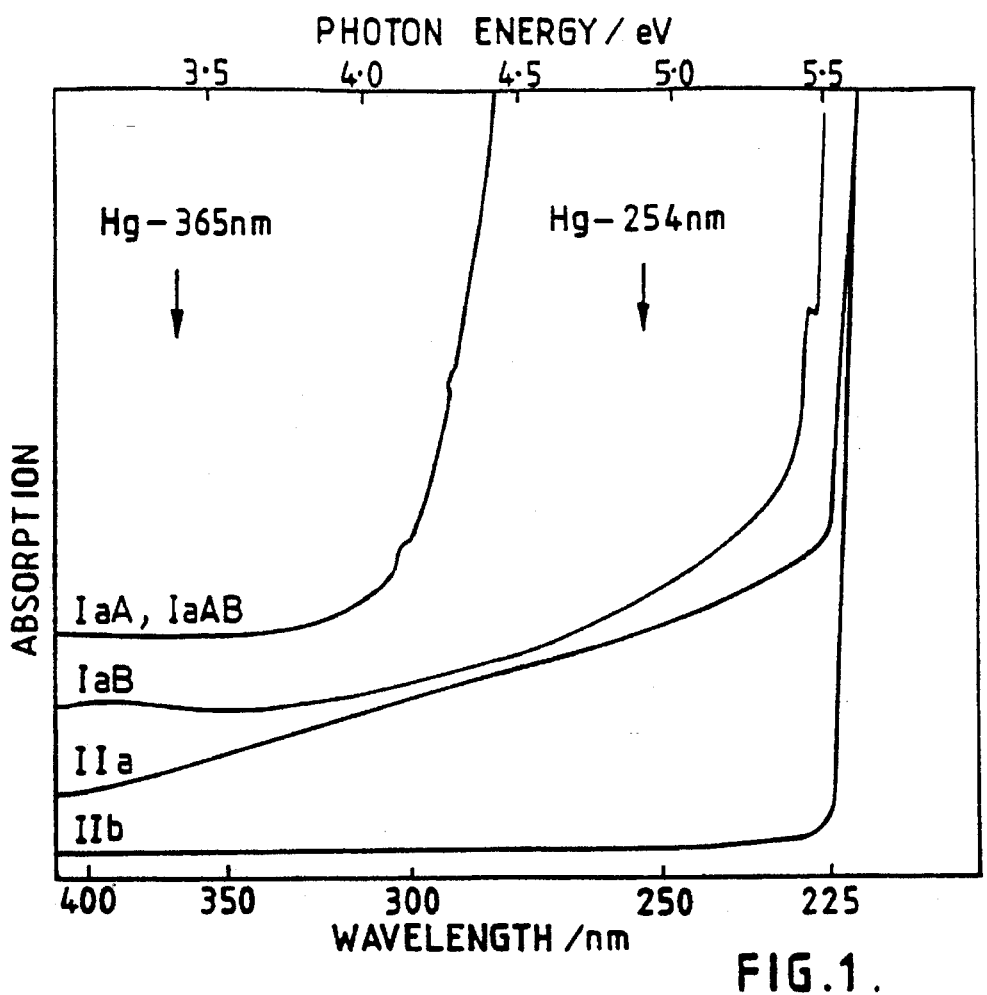
FIG. 1 shows the absorbance of ultra-violet radiation of various wavelengths for different types of diamond.

Diamonds may be classified according to spectroscopic properties. The different types of diamond have their origins in different forms of impurities, which occur in small concentration in the crystal structure. The following classification is commonly used.

Type I—this general type class is defined as the class of diamonds which have a measureable defect induced infrared absorption in the one-phonon region (below 1332 $cm^{-1}$). This general class type is divided into:

Type Ib—which show an optical absorption at about 600 nm continuing with increasing strength into the longwave ultra-violet region due to single nitrogen atoms substituted for single carbon atoms at random throughout the crystal lattice of the diamond. This gives rise to the so-called canary yellow colour shown by some diamonds. Type Ib diamonds represent a non-equilibrated form of diamond. Diamonds are formed at conditions of very high temperature and pressure and if the diamond is maintained at these conditions, impurity nitrogen atoms will tend to aggregate. Natural diamonds are believed to have remained at equilibrating conditions for geologically significant periods of time and accordingly type Ib diamonds are rare in nature. On the other hand, synthetic diamonds are not maintained at equilibrating conditions and accordingly most synthetic diamonds are type Ib.

Type Ia—this class comprises diamonds in which the nitrogen has migrated to form more complex defects. There are two principal forms of nitrogen defect which are found in type Ia diamonds, the A form and B form. The A form comprises pairs of nitrogen atoms on nearest-neighbour substitutional sites. The B form of nitrogen is believed to comprise a complex of four substitutional nitrogen atoms surrounding a vacancy. The ratio of the concentration of A type defects to B type defects varies continuously, the extreme ends of the sequence being labelled type IaA and type IaB. Pure type IaB diamonds are very rare.

Type A centers are associated with a relatively high ultra-violet absorption at wavelengths below about 300 nm. As type A centers are believed to be the result of remaining at equilibrating conditions for a considerable period of time, synthetic diamonds almost never have type A centers. Most naturally occurring diamonds contain both A and B centers and are classified as IaAB. They retain the strong absorption at wavelengths below 300 nm.

Type IIa—This class comprises diamonds in which nitrogen is only present in trace amounts, of the order of 1 ppm. This near absence of nitrogen in diamonds rarely occurs in nature but can be assured in the production of synthetic diamonds.

Type IIb—This is a very rare class of semi-conducting diamonds which contain trace amounts of substitutional boron. Type IIb diamonds are generally natural, but synthetic diamonds having added boron can be produced.

Accordingly, type Ib, IIa and IIb diamonds may be produced synthetically. It is, however, almost impossible to produce type IaA, type IaB or type IaAB diamonds synthetically. All of the latter three types of diamonds encountered would be most likely to be natural.

FIG. 1 shows a series of graphs of absorbance (absorption coefficient per unit path length) in arbitrary units, for a set of typical stones of different class.

All the curves show a steep region at lower wavelengths and a flat region at higher wavelengths, with a relatively sharp junction.

Substantial absorption may be thought of as absorption substantially greater than that found in the flat region, for example 20 times greater, or more.

The invention provides a method of distinguishing natural from synthetic diamonds based upon the short wave ultra violet radiation absorption characteristics. This can be done by identifying the increased absorption below 300 nm associated with A centers. As shown in FIG. 1, the absorption of ultra violet by all the other major types of diamond does not increase much at wavelengths down to about 225 nm, which is a characteristic absorption of all types of diamond. The high absorption associated with type A centers below 300 nm may be detected by comparing a measurement of the ultra-violet absorption at a wavelength above 300 nm with the absorption at a wavelength below 300 nm but greater than the intrinsic diamond absorption at 225 nm. As can be seen from FIG. 1, the ratio of these two measurements will be in the region 1:1 or 2 for diamonds of type IaB, IIA and IIb. However, diamonds of type IaA will have a ratio in the region of 1:20 or 1:100 or more.

Figure 2:
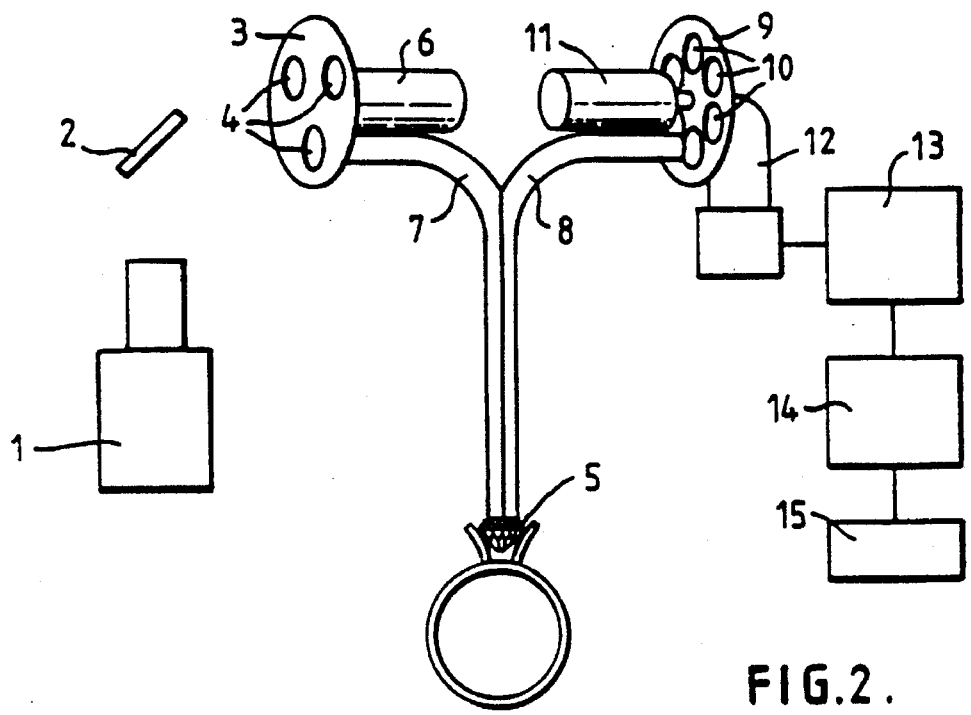
FIG. 2 shows an apparatus for examining a diamond according to the second aspect of the invention.

This technique will identify type IaA diamonds and IaAB diamonds, which represent the vast majority of all natural diamonds. Natural diamonds of type IaB will fail the test. However, the very small occurrence of IaB diamonds in nature renders this defect of minor importance compared with the advantages to be obtained in producing an apparatus which can positively identify the vast majority of natural diamonds. In total, 95% of natural diamonds will pass the test and only 5% will be rejected. These latter can be subjected to other tests. FIG. 2 shows an apparatus for examining diamonds, according to the method of the invention described in relation to FIG. 1 above. This apparatus comprises a radiation source 1 which is suitably a mercury vapor lamp. A mercury vapor lamp produces two strong bands of ultra-violet radiation at 365 nm and 254 nm. These two wavelengths are suitable for the method of the invention described in relation to FIG. 1 above.

Radiation from the source 1 is reflected by mirror 2 through filter wheel 3. The filter wheel 3 has a number of apertures 4 which may also be provided with narrow band pass filters for passing radiation at 365 nm or 254 nm to the diamond. All other wavelengths are blocked by the filter so that the quantity of energy directed on to diamond 5 is not too high. The filter wheel 3 is rotated by motor 6 to present different filters 4 in succession. Radiation passed by filter 4 is transmitted by fiber optic line 7 to the diamond 5.

Preferably, radiation is directed into the table of a cut diamond 5. If the diamond has a brilliant cut, a large quantity of the radiation incident on the table will be reflected out through the table. A second fiber optic line 8 collects radiation transmitted through the diamond in this manner.

A second filter wheel 9 comprises filters 10 for passing radiation at 365 nm or 254 nm. The second filter wheel 9 is altered by motor 11 so that the radiation passed by filter 10 is of the same wavelength as the radiation directed to diamond 5 by filter 4.

The second set of filters is required to exclude radiation produced by fluorescence etc, which would otherwise give an incorrect result. The radiation passed is detected by suitable means 12 such as a photomultiplier tube. The signal produced by the photomultiplier tube 12 is amplified at 13 to provide a signal for a microprocessor 14.

The microprocessor 14 can control the positions of the filter wheels 3 and 9 via motors 6 and 11 and thereby measure the radiation transmitted at both of the wavelengths of interest. The intensities of radiation transmitted at wavelengths of interest are then compared to decide whether the diamond is natural or synthetic. The result may be displayed on a display means 15. The ratio of the intensities of radiation transmitted at the two wavelengths may be taken, the diamond being classified as natural if the ratio of radiation absorbed at 254 nm to that absorbed at 365 nm is greater than 20:1, preferably greater than 50:1, most preferably greater than 100:1.

Figure 3:
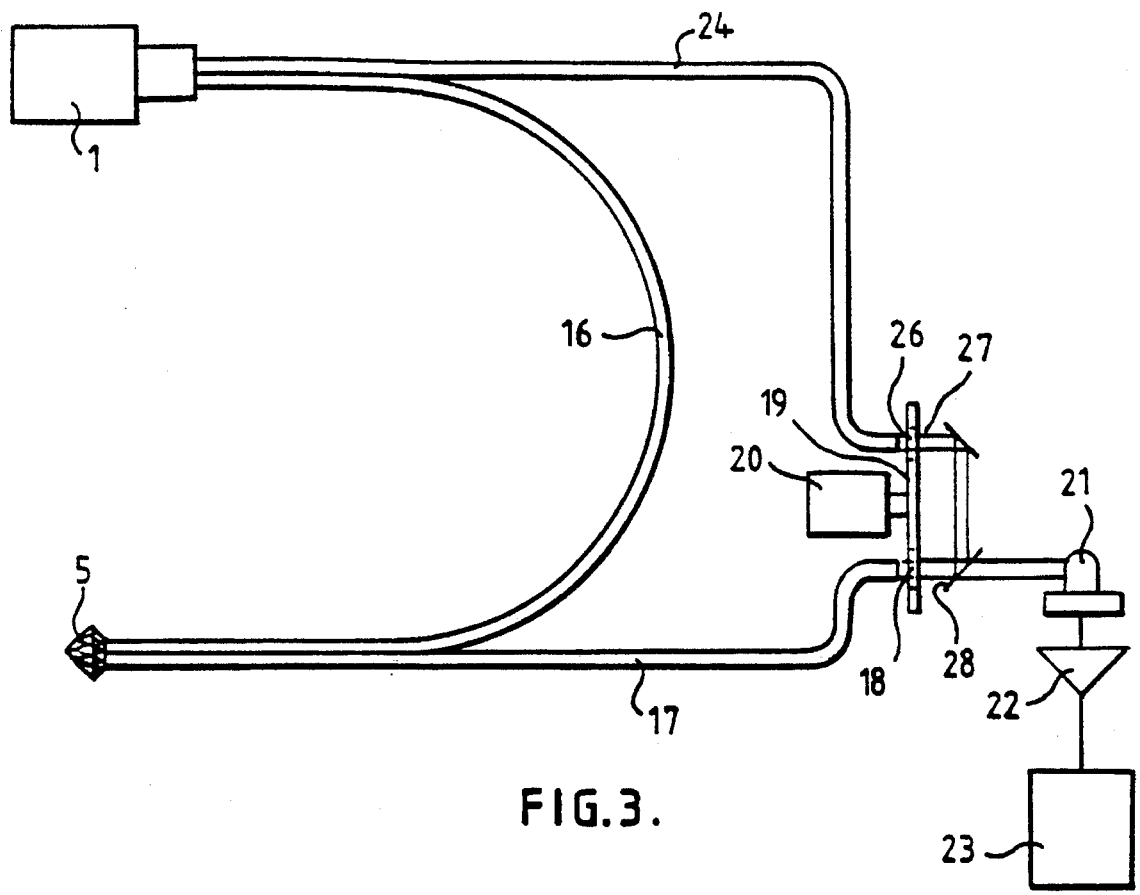
FIG. 3 shows a further embodiment of apparatus for examining a diamond according to the second aspect of the invention.

FIG. 3 shows further apparatus for classifying a diamond according to the method described in relation to FIG. 1 above. In this apparatus, there is no primary filter between the source 1 and diamond 5, radiation being transmitted from the source 1 via fiber optic 16 to the diamond. Radiation transmitted by the diamond is collected by fiber optic 17 and passed through a filter 18 which is a narrow band pass filter passing radiation at a wavelength of 254 nm or 365 nm. The filter 18 is mounted in a filter wheel 19 for quick change between filters of the different wavelengths. The filter wheel 19 is rotated by motor 20. Radiation passed by filter 18 is collected by photomultiplier tube 21, amplified at 22 and processed by a microprocessor 23.

In order to provide information about the intensity of radiation generated by source 1, which may vary with the main voltage applied and thus produce errors, a reference line 24 takes radiation directly from the source 1. The microprocessor 23 may control the position of the filter wheel 19 to present a filter 26 to position 27 to pass radiation of the wavelength of interest (254 nm or 365 nm) from fiber optic 24 to a mirror and beam combiner system 28 while blocking radiation from fiber optic 17. The radiation transmitted by filter 26 is then passed to the photomultiplier tube 21 for providing a signal representative of the illumination intensity.

Figure 4:
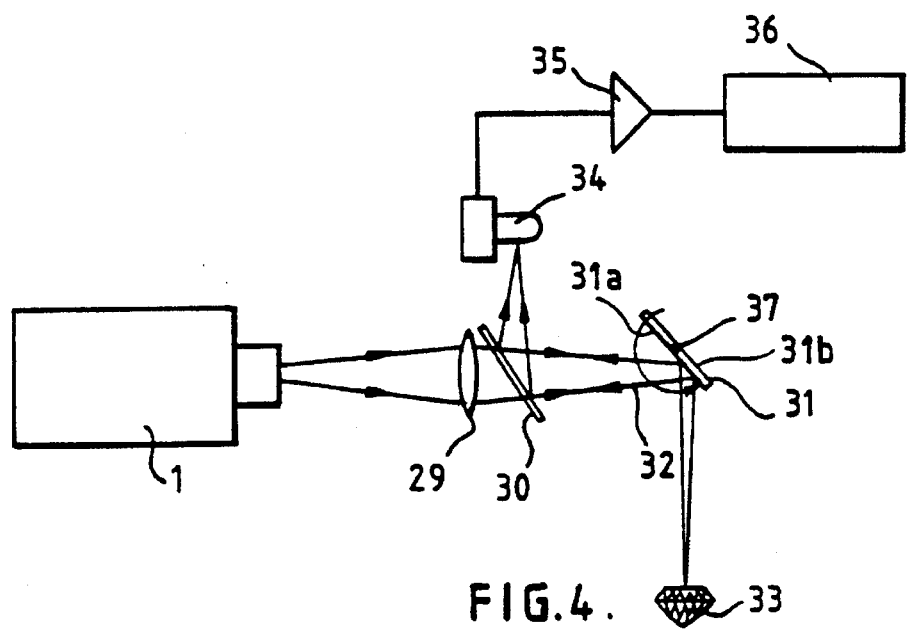
FIG. 4 shows an apparatus for examining a diamond according to the first aspect of the invention.

FIG. 4 shows yet further apparatus for putting the method described in relation to FIG. 1 above into practice, using the idea of the second aspect of the invention. In this apparatus, the means for irradiating an object comprises a source 1 directing radiation through lens 29 and beam-splitting mirror 30 on to a reflective member in the form of a wavelength selective mirror 31. The wavelength selective mirror 31 comprises a wavelength selective surface 31a for reflecting radiation of a wavelength at 254 nm, and a separate wavelength-selective face surface 31b for reflecting radiation at a wavelength of 365 nm on the opposite side of the mirror.

The wavelength selective mirror 31 is rotated so that the different faces 31a and 31b of the mirror 31 are presented to the beam of radiation 32 from the source 1 at different positions, defined by different angles of rotation.

At a first angular position, wavelength-selective surface 31a will be normal to the beam of radiation 32, so that radiation of wavelength 254 nm is reflected back to the beam splitter 30 which directs the reflected radiation to photomultiplier tube 34. The signal produced by the photomultiplier tube 34 is amplified at 35 and stored in the microprocessor 36. Thus the first angular position provides a signal representative of the intensity of radiation produced by illuminating means 1 at 254 nm.

As the mirror rotates, it reaches a second angular position at which surface 31a reflects radiation of the selected wavelength (254 nm) from source 1 onto the table of diamond 33. The radiation interacts with the diamond and a substantial quantity of radiation is transmitted by the diamond and reflected out through the table of the diamond 33 back to the surface 31a. Surface 31a serves to filter out radiation of different wavelengths to 254 nm emanating from the diamond (due, for example, to fluorescence) and reflects light at 254 nm to the beam splitter 30 and thence to photomultiplier tube 34. Thus in the second angular position, a signal or reading is produced representative of the radiation transmitted by the diamond 33 at 254 nm. An aperture (not shown) may be provided between the mirror 30 and wavelength selective mirror 31 or between wavelength selective mirror 31 and object 33 for defining the size of the beam directed to the object or to the detector.

As the mirror continues to rotate, it will present surface 31b to the beam of radiation 32, which surface selectively reflects radiation at 365 nm. At a third angular position radiation of wavelength 365 nm will be reflected back to beam splitter 30 and thence to photomultiplier tube 34. Thus the third angular position will provide a signal or reading representative of radiation produced by the source 1 at 365 nm.

Finally, in a fourth angular position wavelength-selective surface 31b will direct light of a wavelength of 365 nm onto the table of diamond 33, and will reflect radiation emanating from the diamond at a wavelength of 365 nm to the beam splitter 30, so that photomultiplier tube 34 can produce a signal or reading representative of the intensity of radiation transmitted by the diamond at 365 nm.

The signals or information thus provided can be stored by the microprocessor 36 and analyzed as follows. The two measurements of the intensity of radiation produced by source 1 at the different wavelengths may be used to correct the measurements of intensities of radiation emanating from the diamond 33 at the respective wavelengths, to allow for changes in source temperature etc. Then the corrected readings of intensity of radiation emanating from the diamond at the two wavelengths are ratioed, and the diamond is classified in the manner described in relation to the first embodiment, above.

An angle transducer may be provided for detecting the angular position of the selective mirror 31 and giving signals to the microprocessor 36 representative of the wavelength of radiation reflected onto the diamond by the selective mirror 31.

Preferably the selective mirror 31 has the 254 nm selective surface 31a on the opposite surface to the 365 nm selective surface 31b. However, these surfaces could be configured at an angle to each other, the only condition being that each surface will at some position provide illumination intensity information by reflecting radiation back to the beam splitter.

In the apparatus shown i n FIG. 4, the first and third positions correspond to reflective surfaces being normal to the beam of radiation from the source. Alternatively, a further plane back-reflecting mirror may be provided, and the wavelength selective mirror need not be normal to the beam of radiation from the source. The back-reflecting mirror will be placed so that it is normal to the beam of radiation reflected by the wavelength selective mirror in the first position.

Equally, three or more wavelength selective mirrors could be provided for measuring the intensity of radiation transmitted by the diamond at three or more different wavelengths.

The apparatus of any of FIGS. 2, 3 and 4 may be used in the following manner. Instead of taking a single measurement of the radiation emanating from the object at each of the wavelengths of interest and a single measurement of the illumination intensity at each of the wavelengths of interest, all four of these values may be measured in turn in a cycle which is repeated many times over. The microprocessor will store each measurement for each cycle to provide a mass of data which can be statistically analyzed to provide a far more accurate reading than could be produced by a single set of measurements.

This statistical technique is of value generally in that it can cancel out random errors in the illuminating, mounting or detecting system. For example, if the diamond is loosely held in the apparatus (for example by hand) it may be vibrating, leading to errors in the orientation of the table of the diamond or the like. Time variations in the readings can be analyzed statistically by the microprocessor and readings lying outside the bulk of the data may be rejected.

EXAMPLE

An apparatus was set up as shown in FIG. 4. A mercury lamp capable of producing ultraviolet radiation in the band 180 to 350 nm was used. An ultraviolet transmitting lens, for example a fused silica lens as made by Comar Instruments was used. Wavelength selective mirror 31 had wavelength selective coatings 31a and 31b supplied by Tec Optics Limited. Detector 34 comprised a photomultiplier tube of the type R1414 manufactured by Hamamatsu Photonics. Display processing electronics 36 were provided.

The present invention has been described above only by way of example, and modifications can be made within the invention.

We claim:

1. Apparatus for examining an object, comprising means for irradiating the object with radiation and radiation detector means, the irradiating means comprising a reflective member moveable with respect to the detector means, which reflective member has a first position for reflecting the input radiation to the detector means and a second position for reflecting the input radiation onto the object along an irradiation path, wherein in the second position, the reflective member is positioned so that radiation emanating from the object along a path which is substantially coincident with the irradiation path is reflected to the detector means.

2. The apparatus of claim 1, wherein the detector means comprises reflecting means for reflecting radiation from the reflective member to the detector means.

3. The apparatus of claim 2, wherein the reflecting means comprises a beam splitter through which the input radiation is directed onto the reflective member.

4. The apparatus of claim 1, further comprising a radiation source for generating the input radiation.

5. The apparatus of claim 1, wherein the input radiation is polychromatic.

6. The apparatus of claim 1, wherein the reflective member is mounted for rotation about an axis, the first and second positions corresponding to different angular positions about the axis.

7. The apparatus of claim 6, wherein the axis of rotation is normal to the direction of the input radiation.

8. The apparatus of claim 1, wherein the detector means comprises means for comparing the intensity of radiation emanating from the object and the intensity of the input radiation.

9. The apparatus of claim 1, wherein the reflective member comprises wavelength-selective reflective means having a first wavelength selective surface for reflecting a beam of radiation of a first selected wavelength.

10. The apparatus of claim 9, wherein the wavelength-selective reflective means comprises a wavelength selective mirror.

11. The apparatus of claim 9, wherein the wavelength selective reflective means further comprises a second wavelength selective surface for reflecting radiation of a second selected wavelength, so that in a third position the reflective member reflects a beam of radiation of the second selected wavelength to the detector means, and so that in a fourth position the reflective member reflects a beam of radiation of the second selected wavelength onto the object.

12. The apparatus of claim 11, wherein the first selected wavelength is ultra-violet radiation of a wavelength greater than the maximum wavelength at which substantial absorption occurs in a first class of diamonds, and wherein the second selected wavelength is ultra-violet radiation of a wavelength less than the maximum wavelength at which substantial absorption occurs in the first class of diamonds but higher than the maximum wavelength at which substantial absorption occurs in a second class of diamonds.

13. The apparatus of claim 12, wherein the detector comprises means for comparing the intensity of radiation emanating from a diamond at the first and second selected wavelengths.

14. The apparatus of claim 13, wherein the first class of diamonds comprises diamonds of type IaAB or IaA, and the second class of diamonds comprises diamonds which are not of class IaAB nor of class 1aA, and the detector comprises means for providing a signal indicating that the diamond is natural if the intensity of radiation emanating from the diamond at the first selected wavelength is substantially greater than the intensity of radiation emanating from the diamond at the second selected wavelength.

15. The apparatus of claim 11, further comprising a radiation source in the form of a mercury lamp.

16. A method of examining an object, comprising the steps of directing an input beam of radiation onto a reflective member so that radiation is reflected onto radiation detector means, obtaining giving a first signal dependent upon the intensity of the input beam, altering the position of the reflective member with respect to the detector means so that radiation is reflected onto the object along an irradiation path and so that radiation emanating from the object along a path substantially coincident with the irradiation path is reflected by the reflective member to the detector means, obtaining a second signal dependent upon the intensity of radiation emanating from the object, and comparing the first and second signals.

17. The method of claim 16 wherein the input beam is directed onto the reflective member through a beam splitter, the beam splitter reflecting radiation reflected by the reflective member to the detector means.

18. The method of claim 16, wherein the reflective member is rotated about an axis from the first position to the second position.

19. The method of claim 18, wherein the axis of rotation is normal to the direction of the input beam of radiation.

20. The method of claim 16, wherein the reflective member comprises a wavelength selective means so that radiation of a first selected wavelength is reflected.

21. The method of claim 20, further comprising altering the position of the reflective member to a third position in which input radiation of a second selected wavelength is reflected to the detector means, obtaining a third signal dependent upon the intensity of input radiation at the second selected wavelength, altering the position of the reflective member to a fourth position so that radiation of the second selected wavelength is reflected onto the object and so that radiation of the second selected wavelength emanating from the object is reflected by the reflective member to the detector means, obtaining a fourth signal dependent upon the intensity of radiation emanating from the object at the second selected wavelength, and comparing the third and fourth signals.

22. The method of claim 21, wherein the first selected wavelength is greater than the maximum wavelength at which substantial absorption occurs in a first class of diamonds, and the second selected wavelength is substantially lower than the first wavelength but higher than the maximum wavelength at which substantial absorption occurs in a second class of diamonds.

23. The method of claim 22, wherein the diamond is classified as definitely natural if the intensity of radiation emanating from the diamond at the first selected wavelength is substantially greater than the intensity of radiation emanating from the diamond at the second selected wavelength.

24. The method of claim 22, wherein the first class of diamonds comprises diamonds of type IaAB, or IaA, and the second class of diamonds comprises diamonds not of class IaAB nor of class IaA, and wherein the first wavelength is the 365 nm band of a mercury lamp, and the second wavelength is the 254 nm band of a mercury lamp.

25. A method of classifying a diamond as belonging to a first class comprising definitely natural diamonds or to a second class comprising diamonds which are not definitely natural, comprising:

irradiating the diamond with ultra-violet radiation;

obtaining a first signal dependent upon the intensity of radiation transmitted by the diamond at a test wavelength lying between a first wavelength equal to the maximum wavelength at which substantial absorption occurs in the first class of diamonds and a second wavelength equal to the maximum wavelength at which substantial absorption occurs in the second class of diamonds;

normalizing the signal; and classifying the diamond on the basis of the normalized signal.

26. The method of claim 25, wherein the first signal is normalized by obtaining a further signal dependent upon the intensity of radiation transmitted by the diamond at a further wavelength greater than the higher of the first and second wavelengths and classifying the diamond as definitely natural if the first signal is substantially less than the further signal.

27. The method of claim 25, wherein the first class of diamonds comprises diamonds of type IaAB or IaA and the second class of diamonds comprises diamonds not of type IaAB nor of type IaA.

28. The method of claim 26, wherein the further wavelength is the 365 nm band of a mercury lamp, and the test wavelength is the 254 nm band of a mercury lamp.

29. Apparatus for classifying a diamond as belonging to a first class comprising definitely natural diamonds or to a second class comprising diamonds which are not definitely natural, comprising:

means for irradiating the diamond with ultra-violet radiation;

means for providing a first signal dependent upon the intensity of ultra-violet radiation transmitted at a test wavelength lying between a first wavelength equal to the maximum wavelength at which substantial absorption occurs in the first class of diamonds and a second wavelength equal to the maximum wavelength at which substantial absorption occurs in the second class of diamonds;

means for normalizing the signal; and means for providing a signal for classifying the diamond on the basis of the normalized signal.

30. The apparatus of claim 29, wherein the means for normalising the signal comprise means for providing a further signal dependent upon the intensity of radiation transmitted at a further wavelength greater than the higher of the first and second wavelengths.

31. The apparatus of claim 30, wherein the further wavelength is the 365 nm band of a meroury lamp and the test wavelength is the 254 nm band of a mercury lamp.

32. The apparatus of claim 30, wherein the ratio of the first signal to the further signal is taken and the diamond is classified as belonging to the first class if the first signal is less than ⅕ of the further signal.

* * * * *